United States Patent [19]

Alig et al.

[11] 3,939,193

[45] Feb. 17, 1976

[54] D-HOMOSTEROIDS

[75] Inventors: Leo Alig, Liestal; Andor Furst, Basel; Marcel Muller, Frenkendorf, all of Switzerland

[73] Assignee: Hoffmann-La Roche Inc., Nutley, N.J.

[22] Filed: Aug. 29, 1974

[21] Appl. No.: 501,558

[30] Foreign Application Priority Data

Sept. 26, 1973 Switzerland............... 13764/73

[52] U.S. Cl............. 260/457; 260/348 C; 260/405; 260/405.5; 260/468 R; 260/470; 260/476 C; 260/481 R; 260/486 R; 260/488 B; 260/514.5; 260/586 E; 424/303; 424/308; 424/312; 424/314; 424/317; 424/316; 424/331

[51] Int. Cl.².............. C07C 141/12; C07C 49/45

[58] Field of Search.... 260/586 E, 457, 470, 476 C, 260/481 R, 486 R, 488 B, 514.5, 405, 405.5, 468 R

[56] References Cited

UNITED STATES PATENTS

| | | | |
|---|---|---|---|
| 2,860,158 | /1958 | Clinton et al. | 260/488 B |
| 3,686,223 | /1972 | Miller | 260/586 E |
| 3,833,621 | /1974 | Grunwell et al. | 260/397.4 |

*Primary Examiner*—Gerald A. Schwartz
*Attorney, Agent, or Firm*—Samuel L. Welt; Jon S. Saxe; George M. Gould

[57] ABSTRACT

A novel class of D-homosteroids is disclosed. These compounds have potent endocrinal activity, particularly as anti-inflammatory agents.

12 Claims, No Drawings

D-HOMOSTEROIDS

DESCRIPTION OF THE INVENTION

The D-homosteroids provided by the present invention have the following general formula

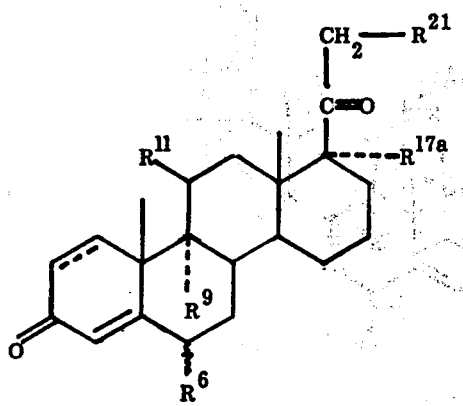

(I)

wherein
- $R^6$ represents a hydrogen, fluorine, chlorine or bromine atom or a methyl group;
- $R^{11}$ represents a fluorine or chlorine atom or a hydroxy group;
- $R^9$ represents a hydrogen, fluorine, chlorine or bromine atom when $R^{11}$ represents a hydroxy group and $R^9$ represents a chlorine or bromine atom when $R^{11}$ represents a fluorine or chlorine atom;
- $R^{21}$ represents a halogen atom or R when $R^{11}$ represents a hydroxy group and $R^{21}$ represents a halogen atom or a hydroxy or acyloxy group or R when $R^{11}$ represents a fluorine or chlorine atom;
- R represents a sulphate or phosphate residue or the residue of a dicarboxylic acid or tricarboxylic acid in the form of a water-soluble salt;
- $R^{17a}$ represents a hydroxy or acyloxy group; and
- the broken line in the 1,2-position denotes an optional bond.

As used in this description and in the accompanying claims, the term "halogen" means fluorine, chlorine, bromine and iodine. An acyloxy group can be derived from a saturated or unsaturated aliphatic monocarboxylic acid, a cycloaliphatic, araliphatic or an aromatic monocarboxylic acid preferably containing up to 15 carbon atoms. Example of such acids are formic acid, acetic acid, pivalic acid, propionic acid, butyric acid, caproic acid, oenanthic acid, undecylenic acid, oleic acid, cyclopentylpropionic acid, cyclohexylpropionic acid, phenylacetic acid and benzoic acid. Especially preferred acyloxy groups are alkanoyloxy groups containing from 1 to 7 carbon atoms. A residue of a dicarboxylic acid or tricarboxylic acid can be derived, for example, from oxalic acid, malonic acid, succinic acid, fumaric acid, malic acid, tartatic acid or citric acid, preferably from succinic acid. The preferred water-soluble salts of such acid residues are the alkali metal salts such as the sodium and potassium salts and the ammonium salts.

It will be appreciated that formula I hereinbefore embraces D-homosteroids of the general formulae (I-1)

and (I-2)

wherein
- $R^6$ represents a hydrogen, fluorine, chlorine or bromine atom or the methyl group;
- $R^{91}$ represents a hydrogen, fluorine, chlorine or bromine atom;
- $R^{92}$ represents a chlorine or bromine atom;
- $R^{110}$ represents a fluorine or chlorine atom;
- $R^{211}$ represents a halogen atom or R;
- $R^{213}$ represents a halogen atom or a hydroxy or acyloxy group or R;
- R represents a sulphate or phosphate residue or the residue of a dicarboxylic or tricarboxylic acid in the form of a water-soluble salt;
- $R^{17a}$ represents a hydroxy or acyloxy group; and
- the broken line in the 1,2-position denotes an optional bond.

Of the D-homosteroids of the foregoing formulae which are substituted in the 6-position, the 6α-isomers are preferred.

According to the process provided by the present invention, the D-homosteroids of formula I hereinbefore are manufactured by
a. hydroxylating a D-homosteroid of the general formula (II)

, wherein
R²¹⁰ represents a halogen atom and
R⁶, R¹⁷ᵃ and the broken line in the 1,2-position have the significance given earlier,
in the 11-position by means of microorganisms or enzymes obtained therefrom, or
b. adding a halogen, hypochlorous or hypobromous acid to the 9,11-double bond of a D-homosteroid of the general formula

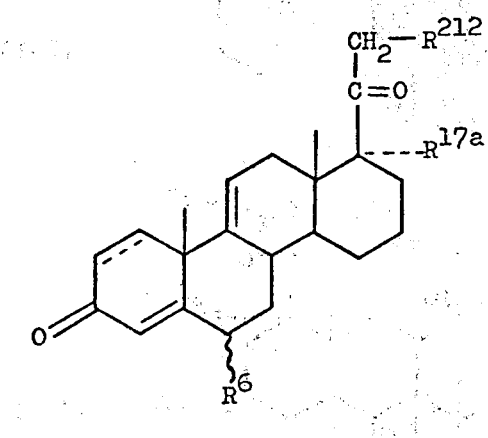

(III)

, wherein
R²¹² represents a hydrogen or halogen atom or R and R, R⁶, R¹⁷ᵃ and the broken line in the 1,2-position have the significance given earlier, or
c. treating a D-homosteroid of the general formula

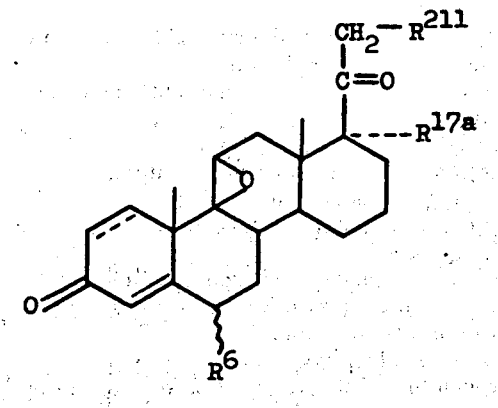

(IV)

, wherein
R²¹¹ represents a halogen atom or R and
R, R¹⁷ᵃ and the broken line in the 1,2-position have the significance given earlier,
with hydrogen fluoride, hydrogen chloride or hydrogen bromide, or
d. dehydrogenating a D-homosteroid of the general formula

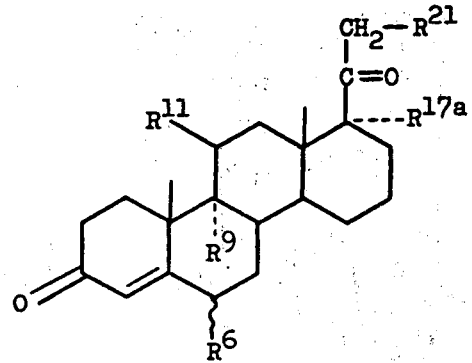

(V)

, wherein
R⁶, R⁹, R¹¹, R¹⁷ᵃ and R²¹ have the significance given earlier,
in the 1,2-position, or
e. halogenating a D-homosteroid of the general formula

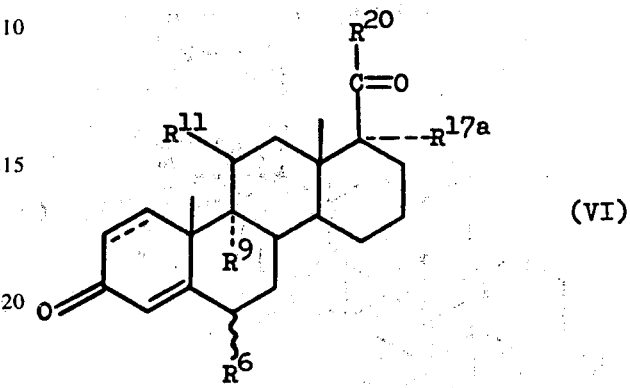

(VI)

, wherein
R⁶, R⁹, R¹¹, R¹⁷ᵃ and the broken line in the 1,2-position have the significance given earlier and
R²⁰ represents a methyl or hydroxymethyl group,
in the 21-position, or
f. treating a D-homosteroid of the general formula

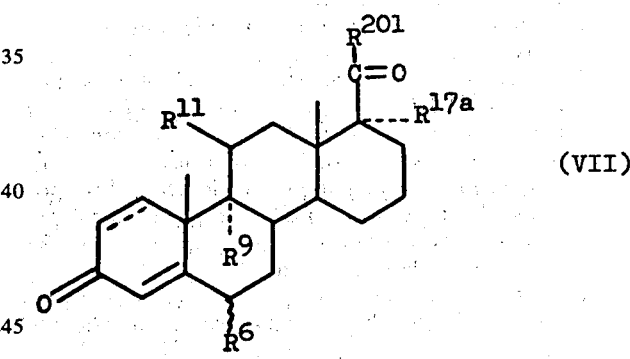

(VII)

, wherein
R⁶, R⁹, R¹¹, R¹⁷ᵃ and the broken line in the 1,2-position have the significance given earlier and
R²⁰¹ represents a hydroxymethyl, halomethyl or diiodomethyl group,
with an acylating agent, or
g. converting the group R²⁰¹ in a D-homosteroid of the general formula

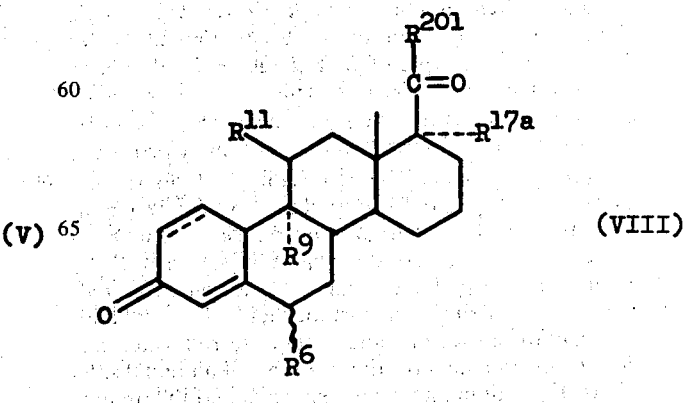

(VIII)

, wherein
R⁶, R⁹, R¹¹, R¹⁷ᵃ and the broken line in the 1,2-position have the significance given earlier and
R²⁰¹ represents a hydroxymethyl, halomethyl or diiodomethyl group,
into the group —CH₂—R' in which R' represents a sulphate or phosphate residue, or
h. saponifying an acyloxy group in a D-homosteroid of formula I in which at least one of R¹⁷ᵃ and R²¹ represents an acyloxy group, or
i. fluorinating, chlorinating or brominating a D-homosteroid of the general formula

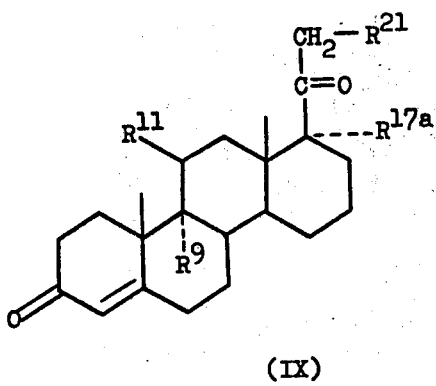

(IX)

or

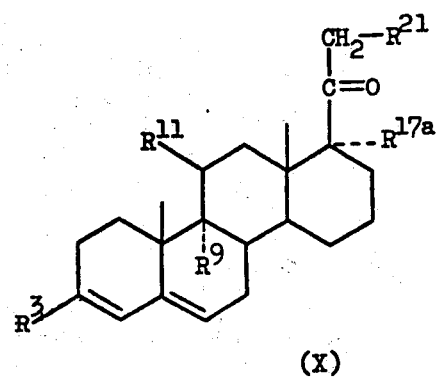

(X)

, wherein
R⁹, R¹¹, R¹⁷ᵃ and R²¹ have the significance given earlier and
R³ represents an esterified or etherified hydroxy group,
in the 6-position and, if desired, isomerising a 6β-isomer obtained to a 6α-isomer, or
k. subjecting a D-homosteroid of the general formula

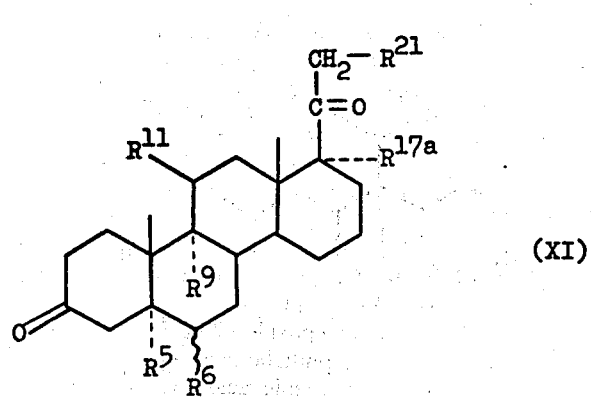

(XI)

, wherein
R⁶, R⁹, R¹¹, R¹⁷ᵃ and R²¹ have the significance given earlier and
R⁵ represents a fluorine, chlorine or bromine atom or a hydroxy group,
to a HR⁵ cleavage, or
L. methylating a D-homosteroid of the general formula

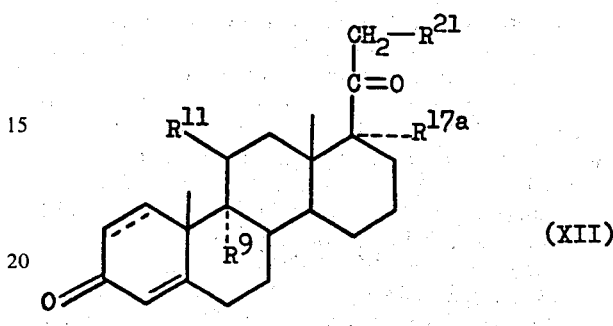

(XII)

, wherein
R⁹, R¹¹, R¹⁷ᵃ, R²¹ and the broken line in the 1,2-position have the significance given earlier,
in the 6-position and, if desired, isomerising a 6β-isomer to a 6α-isomer, or
m. oxidising the 17a(20)-double bond of a D-homosteroid of the general formula

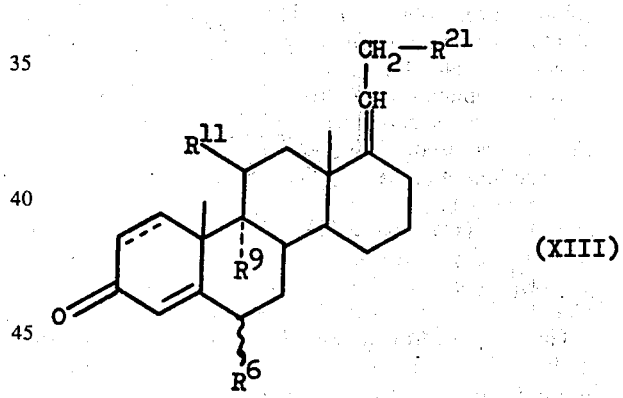

(XIII)

, wherein
R⁶, R⁹, R¹¹, R²¹ and the broken line in the 1,2-position have the significance given earlier,
to the hydroxyketone grouping, or
n. oxidising the 3-hydroxy-Δ⁵ grouping in a D-homosteroid of the general formula

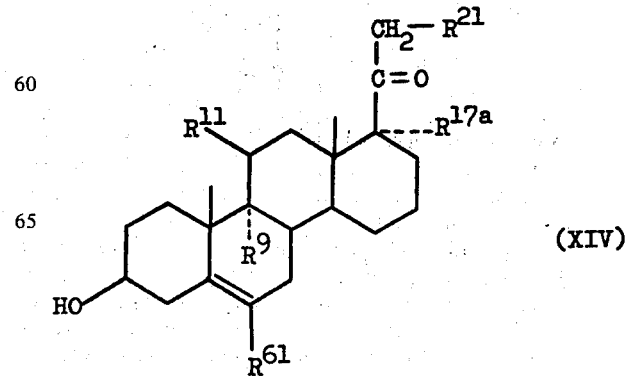

(XIV)

wherein
R⁶¹ represents a hydrogen atom or a methyl group and
$R^9$, $R^{11}$, $R^{17a}$ and $R^{21}$ have the significance given earlier,
to the 3-keto-$\Delta^4$ grouping.

The hydroxylation of a D-homosteroid of formula II in accordance with embodiment (a) of the process can be carried out according to methods known per se for the microbiological introduction of an 11-hydroxy group into steroids. For the 11-hydroxylation there can be used microorganisms of the taxonomic groups fungi and Schizomycetes, especially of the sub-groups Ascomycetes, Phycomycetes, Basidiomycetes and Actinomycetales. There can also be used mutants produced in a chemical manner (e.g. by treatment with nitrite) or in a physical manner (e.g. by irradiation) as well as cell-free enzyme preparations obtained from the microorganisms. Especially suitable microorganisms for the 11β-hydroxylation are those of the genera Curvularia (e.g. C. lunata), Absidia (e.g. A. orchidis and coerula), Colletotrichum (e.g. C. pisi), Pellicolaria (e.g. P. filamentosa), Streptomyces (e.g. S. fradiae), Cunninghamella (e.g. C. bainieri, C. verticellata, C. elegans and C. echinulata) and Pycnosporium.

In embodiment (b) of the present process, a D-homosteroid of formula III is expediently dissolved in a suitable solvent (e.g. an ether such as tetrahydrofuran or dioxane, a chlorinated hydrocarbon such as methylene chloride or chloroform or a ketone such as acetone) and a halogen or hypochlorous or hypobromous acid is allowed to react with the solution. The hypochlorous or hypobromous acid is expediently produced in situ in the reaction mixture; for example, from N-bromo- or N-chloroamides or imides such as N-chlorosuccinimide or N-bromoacetamide and a strong acid, preferably perchloric acid. $Cl_2$, $Br_2$, BrF, ClF or ClBr can be used as the halogen.

Embodiment (c) of the present process is carried out in a manner known per se. Suitably, a D-homosteroid of formula IV is dissolved in an inert solvent and the solution treated with an appropriate hydrogen halide. This embodiment of the process is preferred for the manufacture of 9-fluoro-D-homosteroids of formula I.

The 1,2-dehydrogenation of a D-homosteroid of formula V in accordance with embodiment (d) of the present process can be carried out in a manner known per se; for example, in a microbiological manner or using a dehydrogenating agent such as iodine pentoxide, periodic acid, selenium dioxide, 2,3-dichloro-5,6-dicyanobenzoquinone, chloranil or lead tetraacetate. Suitable microorganisms for the 1,2-dehydrogenation are, for example, Schizomycetes, especially those of the genera Arthrobacter (e.g. A. simplex), Bacillus (e.g. B. lentua and B. sphaericus), Pseudomonas (e.g. P. aeruginosa), Flavobacterium (e.g. F. flavescens), Lactobacillus (e.g. L. brevis) and Nocardia, (e.g. N. opaca).

The halogenation of a D-homosteroid of formula VI in the 21-position in accordance with embodiment (e) of the present process can be carried out by reacting a D-homosteroid of formula VI in which $R^{20}$ represents a methyl group and in which a 3-keto-$\Delta^4$ or 3-keto-$\Delta^{1,4}$ system may be protected (e.g. in the form of a 3-enaminium salt such as a 3-pyrrolidinium-enamine) in acidic solution with elementary chlorine, bromine or iodine. The halogenation can, however, also be carried out starting from a D-homosteroid carrying a hydroxy group in the 21-position, suitably via the mesylate or tosylate, by reaction with an alkali metal halide such as sodium fluoride, sodium chloride or lithium chloride or with carbon tetrachloride in triphenylphosphine/dimethylformamide.

The acylation of a free hydroxy group in the 17a- and/or 21-position of a D-homosteroid of formula VII in accordance with embodiment (f) of the present process can be carried out in a manner known per se by treatment with an acylating agent such as an acyl chloride (e.g. acetyl chloride) or an acid anhydride (e.g. succinic acid anhydride), preferably in the presence of an acid-binding agent such as pyridine. The acylation of a 17a-hydroxy group is expediently carried out in the presence of an acid catalyst such as p-toluenesulphonic acid, $HClO_4$ or HCl.

The selective introduction of an acyl group at the 21-position can be carried out by replacing a 21-halogen atom in a D-homosteroid of formula VII by an acyloxy group; for example, by warming a D-homosteroid of formula VII in which $R^{201}$ represents a halomethyl group with an appropriate alkali metal acylate or ammonium acylate in the presence of the acid corresponding to the acylate (e.g. potassium acetate in glacial acetic acid).

In a particular aspect, a methyl group in the 20-position can first be converted into a diiodomethyl group by reaction with iodine in a manner known per se and the reaction product reacted with an acylating agent (e.g. glacial acetic acid in the presence of a base such as diethylamine).

The introduction of a phosphate or sulphate residue into the 21-position of a D-homosteroid of formula VIII in accordance with embodiment (g) of the present process can be carried out in a manner analogous to that described earlier in connection with embodiment (f) by reacting a D-homosteroid of formula VIII with a phosphate or sulphate (e.g. an alkali metal hydrogen phosphate or hydrogen sulphate or sulphur trioxide in pyridine).

The saponification of an acyloxy group in a D-homosteroid of formula I in accordance with embodiment (h) of the present process can be carried out in a manner known per se; for example, using aqueous-methanolic potassium carbonate solution.

The halogenation of a D-homosteroid of formula IX or X in the 6-position in accordance with embodiment (i) of the present process can be carried out in a manner known per se. A D-homosteroid of formula IX can be halogenated by treatment with a halogenating agent such as a N-haloamide (e.g. N-bromoacetamide) or a N-haloimide (e.g. N-bromosuccinimide or N-chlorosuccinimide) or with elementary bromine or chlorine [see J. Am. Chem. Soc. 72, 4534 (1950)]. The halogenation of embodiment (i)) is preferably carried out by converting a D-homosteroid of formula IX into a 3-enol ester or 3-enol ether of formula X (e.g. the 3-enol acetate) followed by treatment with chlorine or bromine [see J. Am. Chem. Soc. 82, 1230 (1960)], with a N-haloimide [see J. Am. Chem. Soc. 82, 1230 (1960); 77, 3827 (1955)] or with perchloryl fluoride [see J. Am. Chem. Soc. 81, 5259 (1959); Chem. and Ind. 1959, 1317]. In addition, trifluoromethyl hypofluorite can also be used as a fluorinating agent.

The halogenation in accordance with embodiment (i) of the present process can also be carried out by converting a corresponding 4,6-bis-dehydro-D-homosteroid into a 6α,7α-epoxide (e.g. by treatment with a peracid such as perphthalic acid, m-chloroperbenzoic acid or p-nitroperbenzoic acid), treating the 6α,7α-epoxide with a hydrogen halide and cleaving off water from the resulting 7-hydroxy-6-halo-D-homosteroid with the elimination of the 7-hydroxy group and the introduction of a 6,7-double bond. The chlorination can also be carried out using chromyl chloride in methylene chloride or an ether.

Insofar as the halogenation aforesaid yields mixtures of isomers (i.e. mixtures of 6α- and 6β-halo-D-homosteroids), these mixtures can be separated into the individual isomers in accordance with known methods such as chromatography.

The isomerisation of a resulting 6β-halo-D-homosteroid, especially a 6β-(fluoro or chloro)-D-homosteroid, can be carried out by treatment with an acid, especially a mineral acid such as hydrochloric acid or hydrobromic acid in a solvent (e.g. dioxane or glacial acetic acid).

The cleavage $HR^5$ from a D-homosteriod of formula XI in accordance with the embodiment (k) of the present process, namely a dehydration or a dehydrohalogenation, can be carried out in a manner known per se. The dehydration can be carried out by treatment with an acid (e.g. a mineral acid such as hydrochloric acid) or with a base. The dehydrohalogenation can be carried out using a base (e.g. an organic base such as pyridine).

The methylation of a D-homosteroid of formula XII in accordance with embodiment (l) of the present process can be carried out, for example, by converting a D-homosteroid of formula XII into a 3-enol ether (e.g. by treatment with an orthoformic acid ester such as ethyl orthoformate in the presence of an acid such as p-toluenesulphonic acid, if desired with the addition of the corresponding alcohol, or by treatment with a dialkoxypropane such as 2,2-dimethoxypropane in methanol/dimethylformamide in the presence of p-toluenesulphonic acid) and reacting the 3-enol ether with a tetrahalomethane (e.g. $CBr_4$, $CCl_2Br_2$ or $CCl_3Br$ to give the trihalomethyl-$\Delta^4$-3-ketone. The trihalomethyl-$\Delta^4$-3-ketone can be dehydrohalogenated with a base such as collidine to give the dihalomethylene-$\Delta^4$-3-ketone which can, in turn, be converted into the 6α-methyl-$\Delta^4$-3-ketone by catalytic hydrogenation under mild conditions (e.g. using a palladium/strontium carbonate catalyst) and acid isomerization.

A further advantageous procedure for the methylation of 1,2-saturated D-homosteroids of formula XII consists in converting such a D-homosteroid into a 3-enol ether in the manner described earlier, reacting the 3-enol ether in a manner known per se to give a corresponding 6-formyl derivative, reducing the formyl group with sodium borohydride to the hydroxymethyl group and finally dehydrating the product with cleavage of the enol ether to give a D-homosteroid of the general formula

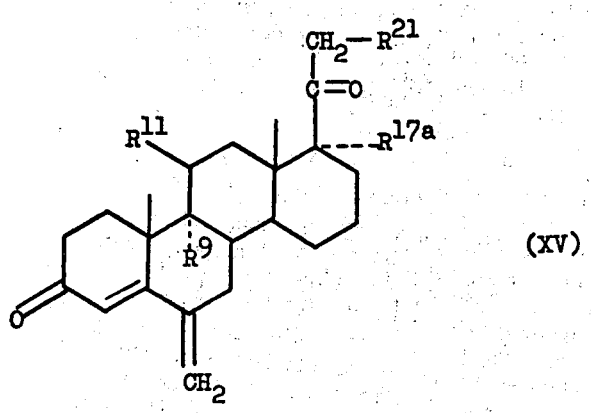

(XV)

wherein
$R^9$, $R^{11}$, $R^{17a}$ and $R^{21}$ have the significance given earlier.

6-Methylene-D-homosteroids of formula XV can also be prepared by conversion of D-homosteroids of formula XII into a 3-enaminium salt (e.g. the 3-pyrrolidinium-enamine), hydroxymethylation using formaldehyde and water-cleavage by means of acids such as p-toluenesulphonic acid. The 6-methylene-D-homosteroids of formula XV can then be hydrogenated in the usual manner using known hydrogenation catalysts to give the corresponding 6-methyl-D-homosteroids.

The isomerisation of a 6β-methyl-D-homosteroid obtained to a 6α-methyl-D-homosteroid can be carried out in the manner described earlier in connection with the isomerisation of a 6β-halo-D-homosteroid.

The oxidation of the 17a(20)-double bond of a D-homosteroid of formula XIII in accordance with embodiment m) of the present process can be carried out, for example, using an oxidising agent such as a tertiary amine N-oxide peroxide in tertbutanol/pyridine in the presence of catalytic amounts of osmium tetroxide. Examples of tertiary amine N-oxide peroxides are N-methylmorpholine N-oxide peroxide and triethylamine oxide peroxide. Alternatively, the oxidation can be carried out using an oxidising agent such as osmium tetroxide or permanganate to give a 17a,20-glycol, further oxidation of the latter using an oxidising agent such as chromium trioxide giving the desired hydroxyketone.

The oxidation of a D-homosteroid of formula XIV in accordance with embodiment n) of the present process can be carried out in a manner known per se; for example, according to the Oppenauer procedure (e.g. using aluminium isopropylate), or using an oxidising agent such as chromium trioxide (e.g. Jones' reagent), or according to the Pfitzner-Moffatt procedure using dimethylsulphoxide/dicyclohexylcarbodiimide (the initially obtained $\Delta^5$-3-ketone requiring subsequent isomerisation to the $\Delta^4$-3-ketone) or using pyridine/sulphur trioxide.

The starting materials required for the foregoing process, insofar as they are not known or described hereinafter, can be prepared in accordance with known methods or in a manner analogous to the methods described in the Examples hereinafter.

The D-homosteroids of formula I hereinbefore possess endocrinal, especially antiinflammatory, activity. They are characterised by having a selective activity, 9,11-dihalo-D-homosteroids of formula I, for example have especially strong topical activity with a weaker systemic activity.

The D-homosteroids of formula I can be used as medicaments; for example, in the form of pharmaceutical preparations which contain them in association with a compatible pharmaceutical carrier. This carrier can be an organic or inorganic inert carrier material suitable for enteral, percutaneous or parenteral administration such as, for example, water, gelatine, gum arabic, lactose, starch, magnesium stearate, talc, vegetable oils, polyalkylene glycols, petroleum jelly and the like. The pharmaceutical preparations can be made up in solid form (e.g. as tablets, dragees, suppositories or capsules), in semi-solid form (e.g. as salves) or in liquid form (e.g. as solution, suspension or emulsions). The pharmaceutical preparations may be sterilised and/or may contain adjuvants such as preservatives, stabilisers, wetting agents, emulsifiers, salts for varying the osmotic pressure or buffers. The pharmaceutical preparations can also contain therapeutically valuable substances other than the D-homosteroids provided by the present invention.

In general, the dosage range in the case of pharmaceutical preparations for topical administration can be about 0.01–1% and the dosage range in the case of preparations for systemic administration can be about 0.1–10 mg per unit of administration.

The pharmaceutical preparations can be prepared in a manner known per se by mixing a D-homosteroid of formula I with non-toxic, solid and/or liquid carrier materials which are customary in pharmaceutical preparations and which are suitable for therapeutic administration (e.g. those carrier materials mentioned hereinbefore) and, if desired, transforming the mixture into the desired pharmaceutical dosage form.

the following Examples illustrate the process provided by the present invention:

EXAMPLE 1

400 mg of 21-acetoxy-17a-hydroxy-D-homopregna-4,9(11)-diene-3,20-dione in 5 ml of chloroform are treated dropwise with 1.2 ml of carbon tetrachloride saturated with chlorine. After 1 hour, the chloroform solution is washed with water, dried and evaporated. After chromatography on silica gel, there are obtained 180 mg of 21-acetoxy-9α,11β-dichloro-17a-hydroxy-D-homopregn-4-ene-3,20-dione of melting point 225°–228°C: UV: $\epsilon_{240}$ = 15800; $[\alpha]_D$ = +150° (c = 0.103% in dioxane).

The starting material can be prepared as follows:

D-Homohydrocortisone acetate is dehydrated with methanesulphonyl chloride in dimethylformamide in the presence of pyridine at an elevated temperature. There is obtained 21-acetoxy-17a-hydroxy-D-homopregna-4,9(11)-diene-3,20-dione of melting point 238°–240°C; $[\alpha]_D$ = +71° (c = 0.104% in dioxane); UV: $\epsilon_{239}$ = 16750.

EXAMPLE 2

In a manner analogous to that described in Example 1, from 400 mg of 21-acetoxy-17a-hydroxy-D-homopregna-1,4,9(11)-triene-3,20-dione there are obtained 50 mg of 21-acetoxy-9α,11β-dichloro-17a-hydroxy-D-homopregna-1,4-diene-3,20-dione of melting point 222°–224°C; UV: $\epsilon_{237}$ = 15300; $[\alpha]_D$ = +142° (c = 0.100% in dioxane).

The starting material can be prepared by dehydrogenating 21-acetoxy-17a-hydroxy-D-homopregna-4,9(11)-diene-3,20-dione in the 1,2-position using 2,3-dichloro-5,6-dicyano-benzoquinone, and melts at 188°–190°C.

EXAMPLE 3

400 mg of 21-acetoxy-17a-hydroxy-D-homopregna-4,9(11)-diene-3,20-dione and 200 mg of N-chlorosuccinimide are stirred for 1 hour at room temperature in 4 ml of a solution of hydrogen fluoride and urea in the ratio of 1:1.25. The mixture is poured on to an aqueous solution of sodium bicarbonate and sodium sulphite and extracted with methylene chloride. The methylene chloride solutions are washed with water, dried and evaporated. After chromatography, there are obtained from methylene chloride/acetone 130 mg of 21-acetoxy-17a-hydroxy-9α-chloro-11β-fluoro-D-homopregn-4-ene-3,20-dione of melting point 238°–239°C; UV: $\epsilon_{238}$ = 16350; $[\alpha]_D$ = +131° (c = 0.102% in dioxane).

EXAMPLE 4

In a manner analogous to that described in Example 3, from 400 mg of 21-acetoxy-17a-hydroxy-D-homopregna-1,4,9(11)-triene-3,20-dione there are obtained 270 mg of 21-acetoxy-9α-chloro-11β-fluoro-17a-hydroxy-D-homo-pregna-1,4-diene-3,20-dione of melting point 266°–268°C; UV: $\epsilon_{237}$ = 15250; $[\alpha]_D$ = +120° (c = 0.104% in dioxane).

EXAMPLE 5

5 g of 11β,17a-dihydroxy-21,21-diiodo-D-homopregn-4-ene-3,20-dione in 50 ml of acetone are treated with 0.5 ml of water, 5 g of dipotassium hydrogen phosphate and 0.3 ml of 85% orthophosphoric acid. The mixture is boiled at reflux in the dark for 4 hours under the atmosphere of a protective gas. 1.8 g of sodium bicarbonate in 25 ml of water are then added and the acetone is evaporated. After acidification with dilute hydrochloric acid, there are obtained 3.1 g of crystalline D-homohydrocortisone 21-phosphate; UV: $\epsilon_{242}$ = 14800.

The starting material can be prepared by iodinating 11β,17a-dihydroxy-D-homopregn-4-ene-3,20-dione in the 21-position in a manner known per se.

EXAMPLE 6

In a manner analogous to that described in Example 5, but using potassium bisulphate in place of dipotassium hydrogen phosphate and 80% sulphuric acid in place of orthophosphoric acid there is obtained D-homohydrocortisone 21-sulphate; UV: $\epsilon_{242}$ = 14200.

EXAMPLE 7

800 mg of 9-fluoro-11β,17a,21-trihydroxy-D-homopregna-1,4-diene-3,20-dione are dissolved in 10 ml of pyridine and the solution is stirred at room temperature for 16 hours with 390 mg of pyridine/sulphur trioxide complex. The product is then treated with 0.02 ml of water, stirred for 2 hours and added dropwise to 100 ml of ether. The precipitate which separates is filtered off under suction, washed with ether and dissolved in 15 ml of absolute methanol. The solution is adjusted to pH 9.85 with 1-N sodium methylate solution, left to stand overnight and again adjusted to pH 9.85. The separated sodium sulphate is filtered off under suction, the filtrate concentrated and treated with ether, the precipitate which separates is filtered off under suction and dried in vacuo. There are obtained 608 mg of sodium (9-fluoro-11β,17a-dihydroxy-D-homopregna-1,4-diene-3,20-dione-21-yl) sulphate; UV: $\epsilon_{238}$ = 14500.

The starting material can be prepared by the reaction of 21-acetoxy-17a-hydroxy-D-homopregna-1,4,9(11)-triene-3,20-dione with hypobromous acid, 9(11)-epoxide formation, opening of the epoxide group with hydrogen fluoride and saponification of the 21-acetoxy group. 9-Fluoro-11β,17a-21-trihydroxy-D-homopregna-1,4-diene-3,20-dione has a melting point of 241°–246°C.

EXAMPLE 8

590 mg of 9-fluoro-11β,17a,21-trihydroxy-D-homopregna-1,4-diene-3,20-dione and 590 mg of triphenylphosphine are dissolved in 6 ml of dimethylformamide and treated with 0.5 ml of carbon tetrachloride. After stirring at room temperature for 1 hour, the mixture is poured on to water and extracted with methylene chloride. The oil obtained after evaporation is taken up in toluene and again evaporated. The residue which remains is chromatographed on silica gel. There are obtained 405 mg of 21-chloro-9-fluoro-11β,17a-dihydroxy-D-homopregna-1,4diene-3,20-dione of melting point 259°–260°C (decomposition); $[\alpha]_D = +110°$ (c = 0.1% in dioxane); UV: $\epsilon_{240} = 15050$.

EXAMPLE 9

500 ml of a sterile nutrient solution containing 5.0% glucose, 0.5% corn steep liquor, 0.2% sodium nitrate, 0.1% potassium dihydrogen phosphate, 0.05% potassium chloride, 0.05% magnesium sulphate and 0.002% iron (II) sulphate are inoculated with a two week old sloping agar culture of Curvularia lunata (NRRL 2380) and shaken for 5 days at 30°C. The thus-obtained pre-culture is used for the inoculation of a 20 liter pre-fermenter charged witn 15 liters of a sterile medium containing 5.0% glucose, 0.25% corn steep liquor, 0.1% sodium nitrate, 0.05% potassium hydrogen phosphate, 0.025% potassium chloride, 0.025% magnesium sulphate and 0.001% iron sulphate. The pre-culture is left to grow at 29°C for 72 hours while stirring (220 revolutions per minute) and with aeration (15 liters of air per minute). 900 ml of the thus-obtained per-culture are transferred to a 20 liter main fermenter containing 14.1 liters of the same medium as the pre-fermenter. The culture is left to grow at 29°C for 24 hours while stirring and with aeration, treated with a sterile-filtered solution of 3.0 g of 17a-hydroxy-21-chloro-D-homo-4-pregnene-3,20-dione in 150 ml of dimethylformamide and fermented for a further 40 hours. The fermentation batch is then filtered and the filtrate and the mycelia are extracted with methyl isobutyl ketone. The extracts are combined and concentrated in vacuo. The residue obtained is chromatographed over a silica gel column and the resulting crude product recrystallised from acetone/hexane to give 21-chloro-11β,17a-dihydroxy-D-homopregn-4-ene-3,20-dione; UV: $\epsilon_{241} = 15900$.

The starting material can be prepared in a manner analogous to that described in Example 8 from 17a,21-dihydroxy-D-homo-pregn-4-ene-3,20-dione (melting point 241°–242°C).

EXAMPLE 10

450 mg of 17a,21-dihydroxy-D-homopregna-4,9(11)-diene-3,20-dione 21-hemisuccinate in 20 ml of dioxane and 5 ml of water are treated with 270 mg of N-bromoacetamide and 1.85 ml of 10% perchloric acid and the mixture is stirred at room temperature for 15 minutes. 1.5 g of sodium sulphite and 30 ml of water are then added. After stirring for a short time, the mixture is extracted with methylene chloride, washed with water, dried and evaporated. There are obtained 540 mg of 11β,17a,21-trihydroxy-9-bromo-D-homopregn-4-ene-3,20-dione 21-hemisuccinate which is uniform according to thin-layer chromatography; UV: $\epsilon_{239} = 14850$.

The starting material can be prepared as follows:
21-Acetoxy-17a-hydroxy-D-homopregna-4,9(11)-diene-3,20-dione in methanolic solution is saponified with potassium carbonate, there being obtained 17a,21-dihydroxy-D-homopregna-4,9(11)-diene-3,20-dione; UV: $\epsilon_{239} = 15800$. This is converted in carbon tetrachloride with succinic acid anhydride in the presence of pyridine at an elevated temperature into 17a,21-dihydroxy-D-homopregna-4,9(11)-diene-3,20-dione 21-hemisuccinate; UV: $\epsilon_{239} = 16200$.

EXAMPLE 11

400 mg of 21-chloro-9,11β-epoxy-17a-hydroxy-D-homopregn-4-ene-3,20-dione are stirred at room temperature for 30 minutes in 10 ml of a solution of 1.25 parts of hydrogen fluoride and 1 part of urea. The mixture is poured on to ice-cold aqueous ammonia and extracted with methylene chloride. The extracts are washed with sodium chloride solution, dried and evaporated. Chromatography of the resiude on silica gel yeilds 21-chloro-9α-fluoro-11β,17α-dihydroxy-D-homopregn-4-ene-3,20-dione; UV: $\epsilon_{239} = 16100$.

The starting material can be prepared as follows:
21-Acetoxy-9α-bromo-11β,17a-dihydroxy-D-homopregn-4-ene-3,20-dione is boiled at reflux for 24 hours in absolute ethanol in the presence of anhydrous potassium acetate. There is obtained 21-acetoxy-9,11β-epoxy-17a-hydroxy-D-homopregn-4-ene-3,20-dione of melting point 226°-228°C; $[\alpha]_D = +51°$ (c = 0.103% in dioxane); $\epsilon_{241} = 14100$.

21-Acetoxy-9,11β-epoxy-17a-hydroxy-D-homopregn-4-ene-3,20-dione is saponified in methanol in the presence of potassium carbonate at room temperature to give 9,11β-epoxy-17a,21-dihydroxy-D-homopregn-4-ene-3,20-dione; UV: $\epsilon_{241} = 14100$. This is treated in dimethylformamide with triphenylphosphine and carbon tetrachloride. There is obtained 21-chloro-9,11β-epoxy-17a-hydroxy-D-homopregn-4-ene-3,20-dione; UV: $\epsilon_{241} = 14200$.

EXAMPLE 12

470 mg of 21-acetoxy-9α,11β-dichloro-17-hydroxy-D-homopregn-4-ene-3,20-dione and 250 mg of selenium dioxide are stirred at reflux for 24 hours under argon in 20 ml of tertbutanol and 0.2 ml of glacial acetic acid. The mixture is filtered and evaporated. THe oil obtained is dissolved in ethyl acetate and washed successively with sodium bicarbonate solution, water, ice-cold ammonium sulphide solution, dilute ammonia, water, dilute hydrochloric acid and water. The solution is then dried over sodium sulphate and evaporated. After chromatography of the residue on silica gel, there is obtained 21-acetoxy-9α,11β-dichloro-17a-hydroxy-D-homopregna-1,4-diene-3,20-dione of melting point 222°–224°C; UV: $\epsilon_{237} = 15300$; $[\alpha]_D = +142°$ (c = 0.1% in dioxane).

The starting material can be prepared by chlorinating 21-acetoxy-17a-hydroxy-D-homopregna-4,9(11)-diene-3,20-dione in a manner known per se.

EXAMPLE 13

0.4 ml of pyrrolidine are added at 60°C under argon to a solution of 1.1 g of 11β,17a-dihydroxy-D-homopregn-4-ene-3,20-dione in 10 ml of methanol. The solution is then left to cool. The enamine which separates is filtered off under suction and dried. To 1.0 g of a solution of this enamine in 50 ml of absolute alcohol containing 0.8 g of hydrogen bromide is added dropwise over a period of 30 minutes a solution of 0.18 ml of bromine in 10 ml of alcohol. The mixture is evaporated. There are obtained 1.3 g of 21-bromo-11β,17a-dihydroxy-3-(N-pyrrolidinium)-pren-4-en-20-one bromide. The foregoing bromide is dissolved in 100 ml of ehtanol and the solution treated with 1 g of potassium carbonate in 20 ml of water and stirred for 1.5 hours at room temperature. The mixture is then poured on to water and extracted with methylene chloride. The methylene chloride solution is washed with water, dried over sodium sulphate and evaporated. Crystallisation from acetone/hexane yields 21-bromo-11β,17a-dihydroxy-D-homopregn-4-ene-3,20-dione; UV: $\epsilon_{242} = 16100$.

The starting material can be prepared as follows:

3β,11β-dihydroxy-D-homoandrost-5-en-17a-one is reacted in dimethyl sulphoxide with sodium hydride and triphenylethylphosphonium bromide to give 3β,11β-dihydroxy-D-homopregna-5,17a(20)-diene of melting point 172°–173°C; $[\alpha]_D = -137°$ (c = 1.04% in dioxane).

Oxidation of the foregoing diene according to the Oppenauer procedure gives 11β-hydroxy-D-homopregna-4,17a(20)-dien-3-one [melting point 160°–161°C; $[\alpha]_D = +96°$ (c = 0.102% in dioxane); $\epsilon_{243} = 15000$] which is converted by oxidation with osmium tetroxide and N-methyl-morpholine oxide/hydrogen peroxide into 11β,17a-dihydroxy-D-homopregn-4-ene-3,20-dione of melting point 213°–215°C; $[\alpha]_D = +104°$ (c = 0.102% in dioxane); $\epsilon_{242} = 16250$.

EXAMPLE 14

880 mg of 21-bromo-11β,17a-dihydroxy-D-homopregn-4-ene-3,20-dione, 600 mg of succinic acid and 1.4 ml of triethylamine are boiled at reflux for 24 hours under argon in 16 ml of acetone. The mixture is poured on to dilute hydrochloric acid and extracted with methylene chloride. The methylene chloride extract is washed with water, dried over sodium sulphate and the solvent removed in vacuo. After crystallisation of the residue from acetone/hexane, there is obtained 11β,17a,21-trihydroxy-D-homopregn-4-ene-3,20-dione 21-hemisuccinate; UV: $\epsilon_{242} = 15900$.

EXAMPLE 15

470 mg of 21-acetoxy-9α-chloro-11β-fluoro-17a-hydroxy-D-homopregna-1,4-diene-3,20-dione in 10 ml of methanol are treated with a solution of 130 mg of potassium carbonate in 2 ml of water while passing argon through the mixture. The mixture is then stirred at room temperature for 1 hour, then poured on to sodium chloride solution and extracted with methylene chloride. The extracts are washed, dried and evaporated. There is obtained pure 9α-chloro-11β-fluoro-17a,21-dihydroxy-D-homopregna-1,4-diene-3,20-dione; UV: $\epsilon_{237} = 15150$.

EXAMPLE 16

2.4 g of 21-acetoxy-11β-fluoro-9α-chloro-17a-hydroxy-D-homopregn-4-ene-3,20-dione in 24 ml of orthoethyl formate and 24 ml of absolute alcohol are treated with 24 mg of p-toluene-sulphonic acid and the mixture is stirred at room temperature for 15 minutes. 0.2 ml of pyridine is then added. The mixture is poured on to water and extracted with methylene chloride. The extracts are washed, dried and evaporated. The crude 21-acetoxy-3-ethoxy-9α-chloro-11β-fluoro-17a-hydroxy-D-homopregna-3,5-dien-20-one is treated under argon in 50 ml of ether with a solution of 4 g of potassium acetate and 4 g of water in 36 ml of acetic acid. 500 mg of chlorine gas are passed into the mixture through a sintered glass filter. The mixture is stirred for a further ca 15 minutes at room temperature, poured on to ice-water, extracted with methylene chloride, washed with water, dried and evaporated. There is obtained a mixture of 21-acetoxy-6β,9α-dichloro-11β-fluoro-17a-hydroxy-D-homopregn-4-ene-3,20-dione as the major product and the corresponding 6α-chloro derivative in a smaller amount. The two isomers are obtained in a pure form by chromatography on silica gel.

EXAMPLE 17

15 g of 21-acetoxy-6β,9α-dichloro-11β-fluoro-17a-hydroxy-D-homopregn-4-ene-3,20-dione in 70 ml of acetic acid are treated with 1 ml of 30% hydrogen bromide in glacial acetic acid and the mixture is stirred at room temperature for 1 hour. After the addition of 2 ml of pyridine, the mixture is evaporated. The residue is worked-up with methylene chloride and sodium bicarbonate solution in the usual manner. After filtration over silica gel, there are obtained 1.3 g of 21-acetoxy-6α,9α-dichloro-11β-fluoro-17a-hydroxy-D-homopregn-4-ene-3,20-dione; UV: $\epsilon_{236} = 14500$.

EXAMPLE 18

500 mg of 21-acetoxy-5α,6β,9α-trichloro-11β-fluoro-17a-hydorxy-D-homopregnane-3,20-dione and 500 mg of dry potassium acetate are stirred in 5 ml of acetone at room temperature for 2 hours. The mixture is poured on to water and extracted with methylene chloride. The extract is washed with water, dried and evaporated. Crystallisation of the residue from acetone/hexane yields pure 21-acetoxy-6β,9α-dichloro-11β-fluoro-17a-hydroxy-D-homopregn-4-ene-3,20-dione; UV: $\epsilon_{239} = 14800$.

The starting material can be prepared as follows:

21-Acetoxy-9α-chloro-11β-fluoro-17a-hydroxy-D-homopregn-4-ene-3,20-dione in methylethyldioxolane is reacted in the presence of a catalytic amount of a strong acid to give 21-acetoxy-3,3-ethylenedioxy-9α-chloro-11β-fluoro-17a-hydroxy-D-homopregn-5-en-20-one. This reacted in chloroform with one equivalent of chlorine in carbon tetrachloride to give 21-acetoxy-3,3-ethylenedioxy-5α,6β,9α-trichloro-11β-fluoro-17a-hydroxy-D-homopregnan-20-one. Subsequent acidic hydrolysis in aqueous acetone gives 21-acetoxy-5α,6β,9α-trichloro-11β-fluoro-17α-hydroxy-D-homopregnane-3,20-dione.

EXAMPLE 19

2 g of 21-chloro-11β-hydroxy-D-homopregna-4,17a-dien-3-one in 20 ml of methylene chloride and 50 ml of tertbutanol are treated with 10 mg of osmium tetroxide, 4 ml of pyridine and 10 ml of a 1.3-N N-methylmorpholine oxide/hydrogen peroxide solution and the mixture is stirred at room temperature for 24 hours. A further 10 mg of osmium tetroxide and 10 ml of reagent solution are then added and the mixture is stirred at room temperature for 24 hours. The mixture is then poured on to water and extracted with methylene chloride. The extract is washed with water, dried and evaporated. Chromatography of the crude product gives 21-chloro-11β,17a-dihydroxy-D-homopregna-4-ene-3,20-dione; UV: $\epsilon_{241} = 15900$.

The starting material can be prepared as follows:

3,11β-Diacetoxy-ndrosta-3,5-dien-17-one in methylene chloride is reacted with ethyleneglycol in the presence of formic acid orthoester and p-toluenesulphonic acid at room temperature to give 3,11β-acetoxy-17,17-ethylenedioxy-androsta-3,5-diene of melting point 183°–186°C; $[\alpha]_D = 112°$ (c = 0.104% in dioxane); $\epsilon_{235} = 19700$.

The foregoing 17-ketal is reduced in tetrahydrofuran/methanol with sodium borohydride to give 11β-acetoxy-17,17-ethylenedioxy-3β-hydroxy-androst-5-ene of melting point 125°–126°C; $[\alpha]_D = 66°$ (c = 0.102% in dioxane).

The ketal obtained according to the preceding paragraph is cleaved in aqueous acetone with p-toluenesulphonic acid to give 11β-acetoxy-3β-hydorxy-androst-5-en-17-one of melting point 193°–195°C; [α]$_D$ = –4° (c = 0.102% in dioxane).

The foregoing 17-ketosteroid is reacted with diemthylsulphoxonium methylide in dimethylformamide to give 21-nor-11β-acetoxy-17,20-epoxy-3β-hydroxy-pregn-5-ene of melting point 155°–156°C; [α]$_D$ = –52° (c = 0.103% in dioxane).

The foregoing epoxide is reacted in alcohol and concentrated ammonia in an autoclave to give 11β-acetoxy-17ξ-aminomethyl-3β,17ξ-dihydroxy-androst-5-ene which is treated with sodium nitrite in glacial acetic acid and water to give 11β-acetoxy-3β-hydroxy-D-homoandrost-5-en-17a-one of melting point 230°–232°C; [α]$_D$ = –121° (c = 0.103% in dioxane).

Saponification of the foregoing 11β-acetate in boiling methanolic potassium hydroxide gives 3β,11β-dihydroxy-D-homoandrost-5-en-17a-one of melting point 234°–236°C; [α]$_D$ = –143° (c = 0.107% in dioxane).

3β,11β-dihydroxy-D-homoandrost-5-en-17a-one in dimethoxyethane is subjected to a Wittig-Horner reaction to give 3β,11β-dihydroxy-D-homopregna-5,17a-dien-21-oic acid ethyl ester which is then reduced using lithium aluminium hydride to give 3β,11β,21-trihydroxy-D-homopregna-5,17a-diene. This diene is reacted with triphenylchloromethane to give 3β,11β-dihydroxy-21-triphenylmethoxy-D-homopregna-5,17a-diene.

The foregoing diene is subjected to an Oppenauer oxidation and subsequent cleavage of the triphenylmethyl ether to give 11β,21-dihydroxy-D-homopregna-4,17a-dien-3-one.

The foregoing 3-one is reacted with triphenylphosphine and carbon tetrachloride in dimethylformamide to give 21-chloro-11β-hydroxy-D-homopregna-4,17a-dien-3-one; UV: ε$_{241}$ = 15500.

EXAMPLE 20

1 g of 21-chloro-3β,11β,17a-trihydroxy-D-homopregn-5-en-20-one is heated to boiling in 12 ml of cyclohexanone and 30 ml of toluene. 1 ml of the solvent is distilled off, 1 g of aluminium tritertbutylate is added and the mixture boiled under reflux for 0.75 hour. The mixture is then poured on to dilute hydrochloric acid and extracted with methylene chloride. The extract is washed with sodium chloride solution and water, dried and evaporated. After chromatography of the residue on silica gel, there is obtained 21-chloro-11β,17a-dihydroxy-D-homopregn-4-ene-3,20-dione; UV: ε$_{241}$ = 15900.

The starting material can be prepared as follows:

3β,11β-dihydroxy-D-homopregn-5,17a-diene is oxidised with osmium tetroxide and N-methyl-morpholine oxide/hydrogen peroxide to give 3β,11β,17a-trihydroxy-D-homopregn-5-en-20-one of melting point 244°–247°C.

The foregoing 20-one is reacted in methanol with iodine in the presence of calcium chloride and calcium oxide to give the 21-diiodide which is converted by boiling with potassium acetate in acetone into 21-acetoxy-3β,11β,17a-trihydroxy-D-homopregn-5-en-20-one.

The foregoing 21-acetate is saponified with potassium carbonate in methanol to give 3β,11β,17a,21-tetrahydroxy-D-homopregn-5-en-20-one which is reacted in dimethylformamide with triphenylphosphine and carbon tetrachloride to give 21-chloro-3β,11β,17a-trihydroxy-D-homopregn-5-en-20-one.

EXAMPLE 21

In a manner analogous to that described in Example 8, from 11β,17a,21-trihydroxy-D-homopregna-1,4-diene-3,20-dione there is obtained 21-chloro-11β,17a-dihydroxy-D-homopregna-1,4-diene-3,20-dione of melting point 248°–249°C; [α]$_D^{25}$ = +125° (c = 0.1% in dioxane); UV: ε$_{243}$ = 14650.

We claim:

1. A D-homosteroid of the formula

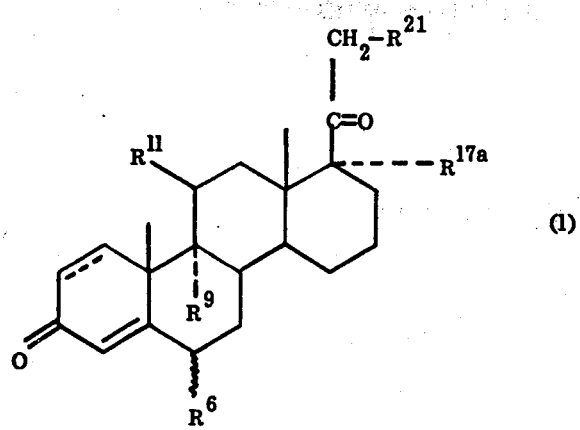

(1)

wherein R$^6$ is hydrogen, fluorine, chlorine, bromine or methyl; R$^{11}$ is hydroxy; R$^9$ is hydrogen, fluorine, chlorine or bromine when R$^{11}$ is hydroxy and R$^9$ is chlorine or bromine when R$^{11}$ is fluorine or chlorine; R$^{21}$ is halogen or R when R$^{11}$ is hydroxy and R$^{21}$ is halogen, hydroxy or hydrocarbon C$_{1-15}$ acyloxy or R when R$^{11}$ is fluorine or chlorine; R is a sulfate or phosphate radical or the radical of a dicarboxylic acid or tricarboxylic acid in the form of a water-soluble salt; R$^{17a}$ is hydroxy or hydrocarbon C$_{1-15}$ acyloxy; and the broken line in the 1,2-position denotes an optional bond.

2. A D-homosteroid of claim 1 of the formula

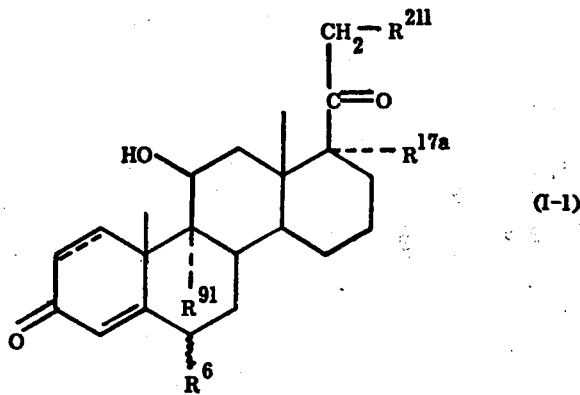

(1-1)

wherein R$^6$ is hydrogen, fluorine, chlorine, bromine or methyl; R$^{91}$ is hydrogen, fluorine, chlorine or bromine; R$^{211}$ is halogen or R; R is a sulfate or phosphate radical or the radical of a dicarboxylic or tricarboxylic acid in the form of a water-soluble salt; R$^{17a}$ is hydroxy or hydrocarbon C$_{1-15}$ acyloxy and the broken line in the 1,2-position denotes an optional bond.

3. The compound of claim 2 which is D-homohydrocortisone 21-phosphate.

4. The compound of claim 2 which is D-homohydrocortisone 21-sulfate.

5. The compound of claim 2 which is sodium (9α-fluoro-11β,17a-dihydroxy-D-homopregna-1,4-diene-3,20-dione-21-yl) sulfate.

6. The compound of claim 2 which is 21-chloro-9α-fluoro-11β,17a-dihydroxy-D-homopregna-1,4-diene-3,20-dione.

7. The compound of claim 2 which is 21-chloro-11β,17a-dihydroxy-D-homopregn-4-ene-3,20-dione.

8. The compound of claim 2 which is 9α-bromo-11β,17a,21-trihydroxy-D-homopregn-4-ene-3,20-dione 21-hemisuccinate.

9. The compound of claim 2 which is 21-chloro-9α-fluoro-11β,17a-dihydroxy-D-homopregn-4-ene-3,20-dione.

10. The compound of claim 2 which is 21-bromo-11β,17a-dihydroxy-D-homopregn-4-ene-3,20-dione.

11. The compound of claim 2 which is 11β,17a,21-trihydroxy-D-homopregn-4-ene-3,20-dione 21-hemisuccinate.

12. The compound of claim 2 which is 21-chloro-11β,17a-dihydroxy-D-homopregna-1,4-diene-3,20-dione.

* * * * *

UNITED STATES PATENT AND TRADEMARK OFFICE
CERTIFICATE OF CORRECTION

PATENT NO. : 3,939,193

DATED : February 17, 1976

INVENTOR(S) : Leo Alig, Andor Furst, Marcel Muller

It is certified that error appears in the above–identified patent and that said Letters Patent are hereby corrected as shown below:

Column 18, line 10-39: Delete claim 1.

Column 18, line 40, delete "of claim 1".

Signed and Sealed this

Twenty-first Day of September 1976

[SEAL]

Attest:

RUTH C. MASON
*Attesting Officer*

C. MARSHALL DANN
*Commissioner of Patents and Trademarks*